US009752219B2

United States Patent
Ma et al.

(10) Patent No.: US 9,752,219 B2
(45) Date of Patent: Sep. 5, 2017

(54) SELF-ADAPTIVE, ULTRA-LOW ELASTIC MODULUS SHAPE MEMORY ALLOYS

(71) Applicant: The Texas A&M University System, College Station, TX (US)

(72) Inventors: Ji Ma, Bryan, TX (US); Ibrahim Karaman, College Station, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 119 days.

(21) Appl. No.: 14/442,494

(22) PCT Filed: Nov. 15, 2013

(86) PCT No.: PCT/US2013/070329
§ 371 (c)(1),
(2) Date: May 13, 2015

(87) PCT Pub. No.: WO2014/078670
PCT Pub. Date: May 22, 2014

(65) Prior Publication Data
US 2016/0281198 A1    Sep. 29, 2016

Related U.S. Application Data

(60) Provisional application No. 61/727,487, filed on Nov. 16, 2012.

(51) Int. Cl.
C22F 1/10    (2006.01)
C22F 1/00    (2006.01)
(Continued)

(52) U.S. Cl.
CPC .............. *C22F 1/006* (2013.01); *A61L 27/06* (2013.01); *A61L 31/022* (2013.01); *C22C 1/02* (2013.01);
(Continued)

(58) Field of Classification Search
None
See application file for complete search history.

(56) References Cited

U.S. PATENT DOCUMENTS 7,947,135 B2 *   5/2011   Fonte ................... A61F 2/30942
148/563
2004/0177904 A1   9/2004   Kajiwara et al.
(Continued)

FOREIGN PATENT DOCUMENTS

JP    2002020849 A    1/2002
JP    2005036273 A    2/2005
(Continued)

OTHER PUBLICATIONS

Translation of JP 2007-051339 from J-Plat Pat, published Mar. 1, 2007.*
(Continued)

*Primary Examiner* — George Wyszomierski
(74) *Attorney, Agent, or Firm* — Conley Rose, P.C.

(57) ABSTRACT

Methods of manufacturing biocompatible, corrosion resistant, self-adaptive, shape-memory titanium-based alloys by using specific ranges of elements in the alloy. Subsequent to melting, the alloy may undergo heat treating, thermo-mechanically processing, and training. Subsequent to training, the alloy has an ultra-low elastic modulus and exhibits self-adaptive, superelastic behavior.

28 Claims, 12 Drawing Sheets

(51) Int. Cl.
- *C22C 1/02* (2006.01)
- *C22C 14/00* (2006.01)
- *C22F 1/18* (2006.01)
- *A61L 27/06* (2006.01)
- *A61L 31/02* (2006.01)

(52) U.S. Cl.
CPC .............. *C22C 14/00* (2013.01); *C22F 1/183* (2013.01); *A61L 2400/16* (2013.01); *A61L 2430/02* (2013.01); *A61L 2430/12* (2013.01); *A61L 2430/24* (2013.01); *A61L 2430/38* (2013.01)

(56) References Cited

U.S. PATENT DOCUMENTS

| | | |
|---|---|---|
| 2005/0011596 A1 | 1/2005 | Tanaka et al. |
| 2006/0228536 A1 | 10/2006 | Chernyshov et al. |
| 2007/0137742 A1 | 6/2007 | Hao et al. |
| 2011/0070121 A1 | 3/2011 | Lee et al. |

FOREIGN PATENT DOCUMENTS

| | | |
|---|---|---|
| JP | 2006265680 A | 10/2006 |
| JP | 2007051339 A | 3/2007 |
| JP | 2011521110 A | 7/2011 |

OTHER PUBLICATIONS

Japanese Office Action dated Aug. 2, 2016, for Japanese Application No. 2015-542824 (4 p.).

Brailovski, Vladimir, et al., "Mechanical Properties of Thermomechanically-Processed Metastable Beta Ti—Nb—Zr Alloys for Biomedical Applications," Materials Science Forum, vol. 706-709, pp. 455-460, Jan. 3, 2012 (7 p.).

Dubinskiy, S.M., et al., "Structure Formation During Thermomechanical Processing of Ti—Nb—(Zr, Ta) Alloys and the Manifestation of the Shape-Memory Effect," The Physics of Metals and Metallography, vol. 112, No. 5, pp. 503-516, Nov. 9, 2011 (14 p.).

Kim, J.I., et al., "Shape Memory Characteristics of Ti—22Nb-(2-8)Zr (at. %) Biomedical Alloys," Materials Science and Engineering, vol. 403, No. 1-2, pp. 334-339, May 13, 2005 (6 p.).

Partial Supplementary European Search Report dated Aug. 22, 2016, for European Application No. 13855181.7 (8 p.).

Canadian Office Action dated May 9, 2016, for Canadian Application No. 2,891,671 (3 p.).

PCT/US2013/070329 International Search Report and Written Opinion dated Feb. 26, 2014 (11 p.).

Canadian Office Action Dated Dec. 12, 2016, for Canadian Application No. 2,891,671 (3 p.).

Extended European Search Report dated Nov. 22, 2016, for European Application No. 13855181.7 (13 p.).

\* cited by examiner

US 9,752,219 B2

SELF-ADAPTIVE, ULTRA-LOW ELASTIC MODULUS SHAPE MEMORY ALLOYS

CROSS-REFERENCE TO RELATED APPLICATIONS

This application is a 35 U.S.C. §371 national stage application of PCT/US2013/070329 filed Nov. 15, 2013, and entitled "Self-Adaptive, Ultra-Low Elastic Modulus Shape Memory Alloys," which claims benefit of U.S. provisional patent application Ser. No. 61/727,487 filed Nov. 16, 2012, and entitled "Self-Adaptive, Ultra-Low Elastic Modulus Shape Memory Alloys," each of which is hereby incorporated herein by reference in its entirety.

STATEMENT REGARDING FEDERALLY SPONSORED RESEARCH OR DEVELOPMENT

This invention was made with government support under 0731133 awarded by the National Science Foundation (NSF). The government may have certain rights in the invention.

BACKGROUND

The present disclosure relates generally to orthopedic and dental implants. More particularly, the present disclosure relates to orthopedic implants such as knee and hip implants as well as dental and surgical screws and plates as well as surgical staples and other implantable devices that are typically manufactured from cobalt chrome or titanium and titanium alloys. Still more particularly, the present disclosure relates to the use of a material to manufacture orthopedic and dental implants that combines strength with flexibility to guard against stress shielding, loosening, and other potential failures in order to increase the life and safety of the implant.

Orthopedic implants may be implanted into people of all ages as well as fitness and activity levels. The implants may be needed, for example, because of joint wear, accidents, or cancer that affects a knee, hip, shoulder, elbow, spine, facial structure, or other musculoskeletal feature. Even with the move towards minimally invasive surgeries for some of these implants, the operation is still intrusive and requires recovery time and in some cases rehabilitation. Implants may need to be replaced due to wear, loosening, or biocompatibility issues. One type of wear is stress shielding which is the reduction in bone density due to the removal of normal stress from the bone by an orthopedic implant.

BRIEF SUMMARY OF THE DISCLOSURE

In an embodiment, a method of making a shape-memory alloy comprising: (a) melting titanium (Ti) and niobium (Nb) to form an alloy; (b) heat treating the alloy formed in (a); (c) thermo-mechanically processing the alloy; and (d) training the alloy, wherein, subsequent to training, the alloy has an effective modulus of elasticity less than 30.0 GPa.

In an embodiment, an ultra-low modulus, corrosion-resistant, shape memory alloy comprising: niobium (Nb); zirconium (Zr); and titanium (Ti), wherein the atomic % of Ti is between about 66 at. % and about 76 at. %; wherein the Nb, Zr, and Ti are melted together to form the shape memory alloy, and wherein the shape memory alloy has an effective modulus of elasticity less than about 30 GPa.

In an alternate embodiment, a method of manufacturing a corrosion resistant, shape-memory alloy comprising: (a) melting titanium (Ti) and nickel (Ni) to form the alloy; (b) heat treating the alloy using a first heat treat process; (c) thermo-mechanically processing the alloy; and (d) training the alloy, to obtain an effective modulus of elasticity less than 40 GPa.

In an alternate embodiment, an ultra-low modulus, corrosion-resistant, shape memory alloy comprising: niobium (Nb); zirconium (Zr); and titanium (Ti), wherein the atomic % of Ti is between about 66 at. % and about 76 at. %; and wherein the alloy has an effective modulus of elasticity less than 30 GPa.

BRIEF DESCRIPTION OF THE DRAWINGS

For a detailed description of the preferred embodiments of the invention, reference will now be made to the accompanying drawings in which.

DETAILED DESCRIPTION OF THE DISCLOSED EMBODIMENTS

Figure 1:
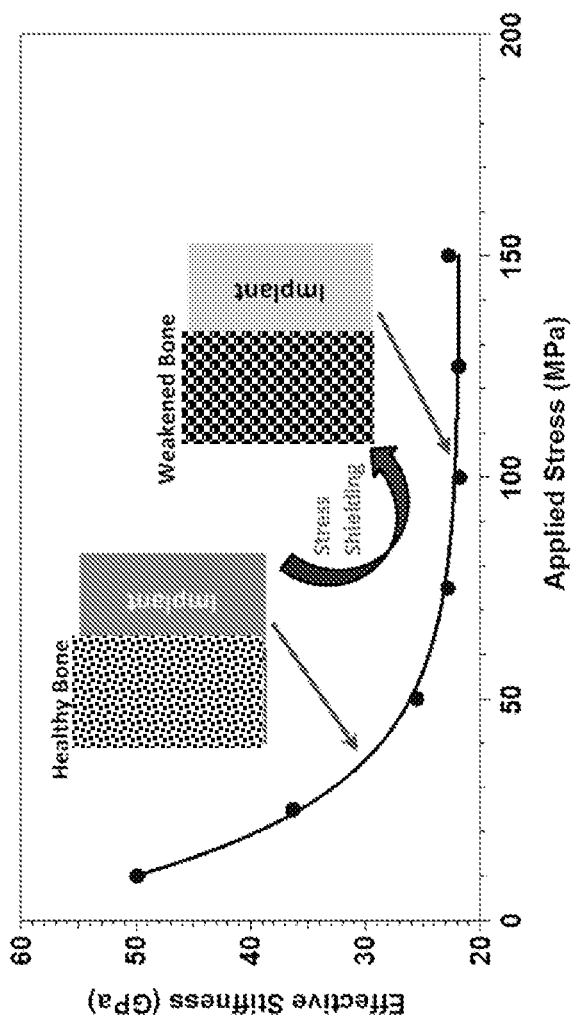
FIG. 1 graph of the effects of stress-shielding on bone and self-adaptive features of the shape memory alloys disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ."

Mechanical Properties of SMAs

Disclosed herein is a method of fabricating shape-memory alloys that have an ultra-low effective elastic modulus and are biocompatible. The elastic modulus refers to a material's tendency to deform when a force is applied, a stiffer material will have a higher elastic modulus than a less rigid material. This material may be used, for example, in medical applications, for example, implanted devices, partially implanted devices, external fixation devices, dental implants, and implantable prosthesis. Implants present concerns with respect to the base material and processing of that material because implants not only need to be durable, to reduce loosening, infection, and subsequent revision surgeries, and biocompatible, but also prevent reduction of bone mass (resorption) and bone quality in the area surrounding the implant. The effective elastic modulus of the implant material, often a stainless steel or Co—Cr alloy, is about 10 times higher than the elastic modulus of the human bone. Since load of the body is then carried with the implant and the surrounding bone in parallel, the stiff implant will carry a large majority of the load. The bone, which is a living tissue that constantly adapts itself to the surrounding, will become weaker as a result of lack of loading, according to Wolff's Law. Over time, this leads to the reduction of bone mass (resorption) and bone quality of bones that surrounds the implant. Bone resorption is the term used to describe the process by which bone is broken down by osteoclasts, this releases minerals and transfers calcium to the blood. Bone resorption caused by stress shielding is frequently observed in patients receiving implants. The reduction of mineral density in the bone surrounding an implant may be up to 50% after three years of implantation. Pronounced bone resorption may occur in 33% of patients 5-13 years after receiving the implant. It should be noted that the terms "implant" and "implants" are used interchangeably here because it is understood that the implantation of an orthopedic implant for a knee, hip, spine, elbow, craniomaxillofacial, etc., may actually involve the implantation of the implant itself, as well as rods, screws, and other components that are affixed to or used in conjunction with the implant. Because these components may be implanted, their biocompatibility may be as important as the primary implant, for example, an acetabular cup, femoral implant, hip stem, or tibial implant.

The initial fabrication and processing of material used for implantable devices, which may comprise titanium (Ti) along with niobium (Nb), nickel (Ni), or zirconium (Zr), must produce an alloy that can be trained to show self-adaptive behavior and an ultra-low effective modulus. Training is the cyclic deformation (loading-unloading) of the alloy at a constant temperature that causes a reduction in its transformation stress ($\sigma_{SIM}$).

An ultra-low modulus is a modulus of elasticity that is below 30 GPa. For purposes of this disclosure, the modulus of elasticity referred to is the effective modulus. In order to be trained, the precursor material must exhibit certain characteristics including: (1) show super elasticity at a temperature greater or equal to the desired operational temperature of the material, (2) the cyclic superelastic deformation of the precursor must allow for a reduction in the transformation stress ($\sigma_{SIM}$) which is defined as the stress where the stress-strain curve is no longer a straight line, and (3) the cyclic superelastic deformation of the precursor must allow for a reduction in the irrecoverable strain ($\epsilon_{irr}$) every cycle. This strain should be zero at the cycle where the minimum $\sigma_{SIM}$ is observed. In addition, the minimum achievable $\sigma_{SIM}$ should be as low as possible. The specific treatment(s) required in order for a precursor material to obtain the above qualities depends on the type and composition of the alloy used. As discussed below, the alloys are heat-treated, which may be a solution-treatment, prior to thermo-mechanical processing and training. The initial heat treat and the subsequent thermo-mechanical processing may comprise a plurality of processing steps which depend on the alloy, the composition, and the desired end use and operating conditions of that end use. Alloys such as those in the shape-memory alloy families of Ni—Ti, Ti—Nb, Cu—Ni—Al, Cu—Zn—Al, Cu—Mn—Al, Fe—Ni—Co—Al, and Fe—Ni—Mn—Al may meet these requirements.

While the specific processing routes may be determined by alloy, composition, and end use, the training process can still be generalized by several principles. First, training may be performed in a similar load condition as the expected load condition of the material in application. For example, if the material is expected to carry tensile load in application, training should be done in tension. Second, training may be performed to a strain level greater than the expected maximum strain the material is expected to experience in application. For example, if a material is expected to deform to a maximum of 3% strain in application, it should be trained to a strain greater than 3%. Third, a higher training strain results in a faster reduction in $\sigma_{SIM}$. Fourth, the maximum training strain should not exceed maximum superelastic strain by about 2%, in some embodiments, the maximum may be about 1%. Fifth, training cycles should be carried out until the minimum $\sigma_{SIM}$ is obtained, or a desired level of $\sigma_{SIM}$ has been reached. And finally, the training may be carried out at a temperature slightly higher than the expected operating temperature of the material.

The alloys described herein are self-adaptive, biocompatible, corrosion resistant, shape-memory alloys. Self-adaptive is a term used to describe the response of a material to changing conditions, and this is a property that may be desired in products that undergo cyclic strain, or other parts where these characteristics are desirable, such as orthopedic and dental implants or engine components. The reason that self-adaptive behavior may be desired from an alloy in these cyclic stress situations is because of stress shielding. In the case of orthopedic and dental implants, stress shielding may occur because the implant material carries a larger portion of the load than the surrounding bone, due to the higher elastic modulus of the implant. For implants of conventional metals and alloys, the effect of stress shielding will naturally intensity as bone resorption and loss leads to further transfer of load to the implant, and accelerates the bone loss process. When the bone gets weaker, the implant will carry more of the load. If the implant can put more weight on the bone, the bone is less likely to become weaker. Stress shielding occurs when the bone doesn't see enough load, so if an implant can transfer load to the bone the bone may not weaken as quickly. However, as shown in the cyclically-softened Ti—Nb shape memory alloy in FIG. 1, if bone loss occurs that leads to the transfer of more loads to the implant, the effective elastic modulus of the implant will be reduced and return the load back to the bone, preventing further degradation, and help the bone grown and heal itself. Bone in a healthy person will remodel in response to the loads it is placed under, if a load on a bone decreases, the bone will become less dense and weaker because there is no stimulus for continued modeling that is required to maintain bone mass. The stress-dependence of the effective modulus allows the implant to adjust its properties based on its operating environment: if a higher than desired level of load is carried by the implant, it will automatically reduce its effective modulus to transfer load back to the surrounding. Because the alloy responds, sometimes immediately, to weakening of the bone due to stress shielding by reducing its effective stiffness, the self-adaptive behavior may counteract and slow the progression of bone loss by helping the bone to heal itself.

Phase Transformation and Mechanical Properties

Martensitic transformation is a solid-to-solid phase transformation that occurs through a coordinated shear movement of atoms over very short (on the order of angstroms) distances where atoms retain their neighboring relationship with one another. The high temperature phase, austenite, transforms to a low temperature phase, martensite, upon cooling. Because the crystal structure of austenite is different than that of martensite, it is possible to obtain a macroscopic shape change that accompanies the transformation.

In the absence of stress, austenite transforms to twined martensite upon cooling in order to accommodate strain caused by a change in crystal structure. The twinned martensite is composed of multiple twin-related lattice correspondence variants. When stress is applied, the martensite may detwin, resulting in a single lattice correspondence variant structure and a net shape change. When martensite forms inside austenite, the difference in their crystal structures generates large local strain. This strain is large enough so it cannot be purely accommodated elastically. Instead in SMAs, the strain is accommodated by producing a twinned martensite structure. When the higher symmetry austenite transforms to the lower symmetry martensite, it may do so in several "ways" called martensite lattice correspondence variants. The number of such variants that can be formed is determined by the crystal structures of the martensite and the austenite. By forming a structure of twin-related lattice correspondence variants, the martensite is able to accommodate a large portion of the strain associated with the change in crystal structure. Under an external biasing stress, certain variants become energetically favored and form or grow at the expense of others in a process known as martensite re-orientation. In addition, the martensite may also detwin, where analogously, the lattice correspondence variant favored under stress grows at the expense of others. Both martensite re-orientation and detwinning results in the macroscopic shape change, and give rise to the shape memory behavior and superelasticity.

The martensitic transformation can be induced both thermally and through the application of stress. In other words, application of stress and reduction in temperature both act as driving forces for the austenite→martensite transformation. In fact, there is a linear relationship between the two. This relationship is derived from the thermodynamics relationships of phase transformation and is called the Clausius-Clapeyron relationship. Roughly, it states that $$\frac{d\sigma}{dT} = \text{constant.}$$

The deformation response of SMAs depends on the testing temperature relative to the transformation temperatures martensitic start ($M_s$), martensitic finish ($M_f$), austenitic start ($A_s$), and austenitic finish ($A_f$), of the alloy. If the material is deformed below the $M_f$ temperature in a self-accommodated martensite structure, then the strain is accommodated by the growth of one variant favored by the stress in the expense of others, as well as detwinning. Since all martensite variants are equally stable in the absence of external and internal stresses, the martensite stays in the re-oriented and detwinned state, and remains in the deformed shape after unloading. When heated above $A_f$ temperature after unloading, all martensite transforms back to austenite. When the austenite is once again cooled below $M_f$, the martensite will again form in a self-accommodated state, and all deformations from detwinning are recovered in the absence of plasticity; this is the one-way shape memory effect. This means that the austenite shape of the alloy is "remembered", and the material can return to this shape even after deformation in the martensite state. This ability enables "deployable bio-devices" that are deployed in a deformed martensite state to facilitate easy installation, and then morphs into the desired shape as it is warmed to body temperature.

On the other hand, if sufficient stress is applied in the austenite state, the austenite may transform into martensite in a single-variant configuration, which results in a macroscopic shape change. When the stress is removed, however, the martensite becomes unstable and reverts to austenite, and recovers this change in shape. This effect is known as superelasticity, the material is able to sustain a large amount of recoverable strain, from 5%-25%, depending upon the alloy. The flexibility has been utilized in a number of biomedical applications such as orthodontic arch wires and temporarily bone staples and braces to promote healing.

Conventionally, Ni—Ti SMA (nitinol) is thought to possess much lower elastic modulus than currently used implant alloys. In the austenite state, nitinol is reported to have an elastic modulus of between 60-80 GPa, while in the martensite state, this number is reported to be 30-60 GPa. The reportedly low stiffness would appear to reduce the risks of stress shielding and makes Ni—Ti an attractive implant material: not as a shape memory alloy, but simply a metallic alloy with low elastic modulus. However, the reported low martensite modulus of nitinol is an apparently misleading one. Numerous neutron diffraction, atomistic simulation, and synchrotron diffraction work has shown that the actual elastic modulus of the martensite is well over 100 GPa. The reason that a small modulus is observed in a conventional stress-strain diagram is the simultaneous activation of martensite reorientation and martensite detwinning alongside elastic deformation. Unfortunately, strain caused by martensite reorientation and detwinning does not appear to recover upon unloading, so even at very low applied stress level, irrecoverable strain can be observed in a stress-strain diagram of nitinol in the martensite state. This means that nitinol may not be able to be used in the martensite state as an implant material as it will continuously undergo permanent shape change as stress is applied. However, instead of irreversible mechanisms such as martensite reorientation or detwinning, it may be possible to activate a reversible deformation mechanism, such as stress-induced phase transformation, concurrently with elastic deformation to reduce the effective modulus of the alloy. In most shape memory alloys, including nitinol, the stress required to activate stress-induced phase transformation are quite high (~200-300 MPa). Since implants do not typically experience such loads, it is apparently not possible to take advantage of this mechanism.

Ti—Nb Shape Memory Alloys

Ti SMAs with bio-inert constituents such as the Ti—Mo, and the Ti—Nb systems may be suitable for applications such as implants and others where shape-memory properties are needed in conjunction with an ultra-low effective modulus of elasticity. In addition, ternary alloys may be viable with the addition of Ag, Ga, and Sn to the Ti—Mo system, and Al, Ga, Ge. The addition of Pd, Si, Sn, Ta, and Zr to the Ti—Nb alloys may also produce the self-adaptive behavior that may be preferred for these shape-memory alloys. $Ti_{72}Nb_{22}Zr_6$ currently exhibits the highest total recoverable strain of 4.5% among all Ti alloys other than Ti—Ni. Ti—Nb alloys may be preferred by industries such as the biomedical industry due to high biocompatibility, corrosion resistance, superior workability, and relatively low Young's modulus.

In addition to a reduction of the effective modulus, the mechanical and superelastic properties of the Ti—Nb SMAs must be sufficiently improved through work hardening, grain refinement, and crystallographic texture engineering in order to be considered a feasible material for structural implants. In the experiments in this disclosure, severe plastic deformation technique Equal Channel Angular Extrusion (ECAE) and training were used to achieve the lowered effective modulus as well as the self-adaptive, superelastic, shape-memory properties discussed herein.

Low-cycle and Functional Fatigue in Shape Memory Alloys

As SMAs experience forward-reverse transformation cycles multiple times, their shape memory and superelastic properties undergo changes caused by defects that are generated and modified by the transformation. These changes may include an increase or decrease in transformation temperatures, reduction of stress, reduction of thermal hysteresis, accumulation of irrecoverable strain, and changes in the hardening rate of the stress-strain diagram. Traditionally, cyclic functional fatigue may be undesirable since it alters the properties of the alloy, causing it to deviate from its desired engineering response. However, functional fatigue can generally be stabilized after a number of transformation cycles, such that further cycles no longer affect properties appreciably, and in many applications. SMA components are subjected to such a stabilization process known as training to improve the predictability of the alloy response.

These transformation-induced changes are caused either by the generation of defects or retained martensite during transformation. As the interface between martensite and austenite form and move, defects are generated at the boundary because the lattice mismatch between the two phases, causing dislocations to form to relieve the accumulated internal stress. However, the precise effect of cyclic functional fatigue depends on the method by which the transformation occurs. When a SMA transform from changes in temperature under stress-free conditions, the transformation temperatures generally decrease. As transformation takes place, dislocations are generated at the interface between martensite and austenite. However, since no stress is applied, martensite is formed in the self-accommodated state and the stress field from the generated defects is randomly oriented. This means that no specific martensite variant is favored by the defects and as a result, the defects hinder the phase transformation by acting as obstacles to the movement of the phase front in subsequent transformation cycles. Austenite is stabilized over the martensite and transformation temperatures are decreased. On the other hand, if thermal-induced transformation occurs under applied stress, or if transformation is stress-induced, transformation cycles will increase the transformation temperatures of the alloy. Dislocations formed during these cycles are oriented and favors specific martensite variants, and thus the energy required to active the transformation of these variants are reduced, and martensite becomes stabilized compared to austenite. In structural implant applications, SMAs are used for their superelasticity. The focal point of present study is therefore the cyclic response of stress-induced phase transformation. Stress-induced phase transformation cycles cause three main changes in the stress-strain response of the alloy: 1) the transformation stress will gradually decrease with the number of cycles due to the increase in transformation temperature; 2) transformation stress hysteresis will be reduced, and 3) irrecoverable strain will be accumulated.

The aforementioned changes in the superelastic properties due to low-cycle functional fatigue have largely been explained by the generation of dislocations at the phase boundaries, similar to the explanation used for thermal-induced transformation of SMAs. However, retained martensite may play a role in the changes in superelastic behavior. When the material is loaded again, it no longer requires nucleation of martensite since martensite already exists in the matrix. Instead, the retained martensite simply grows. Since nucleation is reduced or eliminated, the energy barrier for the austenite→martensite transformation is significantly reduced, thus the stressed required to trigger stress-induced transformation is also reduced. The martensite is retained by dislocations, but other mechanisms, such as point defects and precipitates, have also been suggested as possibilities.

Experimental Results

In the experiments discussed below, the effect of superelastic cycling was used as a tool to reduce the effective modulus of the alloy. In order to create an ultra-low elastic modulus, alloys were fabricated from elements of 99.99% purity by vacuum arc melting and cast into rectangular billets of 0.75"×0.75"×5". The billets were then solution treated at 1000° C. for 1 hour and water quenched. Two Ti—Nb-based shape memory alloy compositions were evaluated, a binary $Ti_{74}Nb_{26}$ (at. %) and a ternary $Ti_{72}Nb_{22}Zr_6$ (at. %) alloy. Equal channel angular extrusion (ECAE) of the Ti—Nb billets was performed using a 250-ton MTS hydraulic press with a custom extrusion tool constructed from Inconel 718, a precipitation hardened nickel-chromium alloy. The tool is an L-shaped channel with a sharp 90° angle with a square cross-section of 0.75". Because of the low strength and superb ductility of the Ti—Nb and Ti—Nb—Zr alloys in the solution-treated state, the extrusion was easily carried out at room temperature. An extrusion rate to 0.01 in $s^{-1}$ allowed the extrusions to proceed without incident.

The binary $Ti_{74}Nb_{26}$ alloy was processed using two different ECAE routes. The first route (ECAE 1A) comprised one extrusion pass at room temperature, and the second route (ECAE 4Bc) comprised four extrusion passes with clockwise 90° rotation of the billet about the extrusion axis after each test at room temperature. The ternary $Ti_{72}Nb_{22}Zr_6$ alloy was extruded only via the first route at room temperature.

Shape memory and superelastic behavior did not appear in specimens extruded at room temperature without further heat treatments. A short intermediate temperature annealing process was then performed to allow some microstructure recovery. A plurality of heat treatments with temperatures between 400° C. to 800° C. and durations between 5 minutes to 1 hour were carried out on the as-extruded specimens, and all specimens were water-quenched. Table 1 summarizes all the post-extrusion annealing heat treatments studied that showed promising shape memory properties and reflects that an additional precipitation heat treatment at 300° C. for 1 hour was performed on the annealed specimens A610 and C610, the alloy notations are correlated below to the mechanical process and heat treatment received by each sample.

TABLE 1

| Mechanical Process | Heat Treatment | Notation |
|---|---|---|
| ECAE 1A | 600° C. 10 Minutes | A610 |
|  | 600° C. 1 Hour | A61H |
| ECAE 4Bc | 600° C. 10 Minutes | C610 |
|  | 600° C. 5 Minutes | C65 |
|  | 500° C. 10 Minutes | C510 |

Figures 2A, 2B:
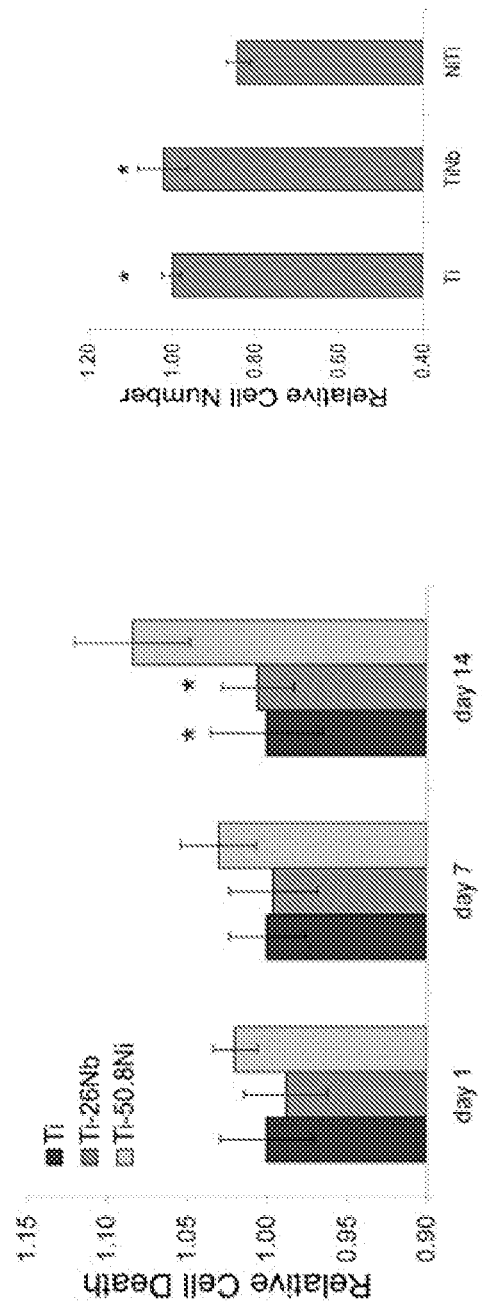
FIGS. 2A and 2B are cytotoxicity results from Ti and Ti-based alloys.

In addition to the mechanical properties and behavior desired from these alloys, properties such as biocompatibility and corrosion-resistance are preferred and may be necessary, as such, cytotoxicity and corrosion results are discussed herein. FIGS. 2A and 2B show the result of the cytotoxicity experiments on pure titanium, $Ti_{74}Nb_{26}$, and $Ni_{50.8}Ti_{49}$. The results indicate that the $Ni_{50.8}Ti_{49}$ SMAs were somewhat more toxic than the $Ti_{74}Nb_{26}$ and pure Ti samples, whereas $Ti_{74}Nb_{26}$ and Ti were similar in their cytocompatibility. The cytotoxicity of the corrosion products varies widely for cells of different organisms. For example, exposure of human blood lymphocytes to bulk Ni—Ti surface treated by autoclaving in steam or water evoked little adverse cellular response, while rat blood lymphocytes exposed to similarly processed Ni—Ti actually showed an improved stimulation in cell proliferation. On the other hand, when exposed to porous Ni—Ti, which has higher surface area, the proliferation of the rat lymphocyte was almost completely suppressed, similar to the effect of pure nickel, while the reduction of human lymphocytes is only about 30%. The cells (NIH/3T3) used in the present study is a mouse fibroblast line, so it is possible that for human cells, the cytotoxicity response may be different. One certainty among the sometimes contradictory findings on the cytotoxicity of Ni—Ti in published literature is that higher nickel release and higher concentration of nickel atoms at the surface of the alloy are correlated with reduced cell viability. Therefore, it is important to concentrate on the specific mechanism of metal release on cytotoxicity; this is the reason that we chose to conduct an indirect contact study. In this case, the results are expected to depend only on the identity and amount of metallic corrosion products and minimize the direct effect of surface features on cell viability since cells do not come in direct contact with the specimen. Since both the Ni—Ti and Ti—Nb specimens were polished to the exact same final finish (0.05 μm), the surface roughness, the surface area of the two specimens are expected to be similar.

Figure 3B:
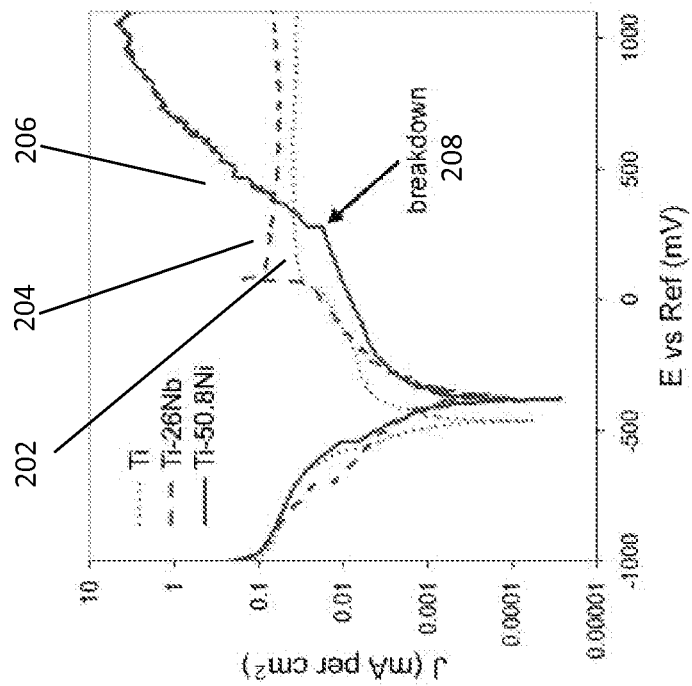
FIGS. 3A and 3B are potentiodynamic polarization graphs of corrosion resistance in saline (3A) and modified Hank's solution (3B) environments.
Figure 3A:
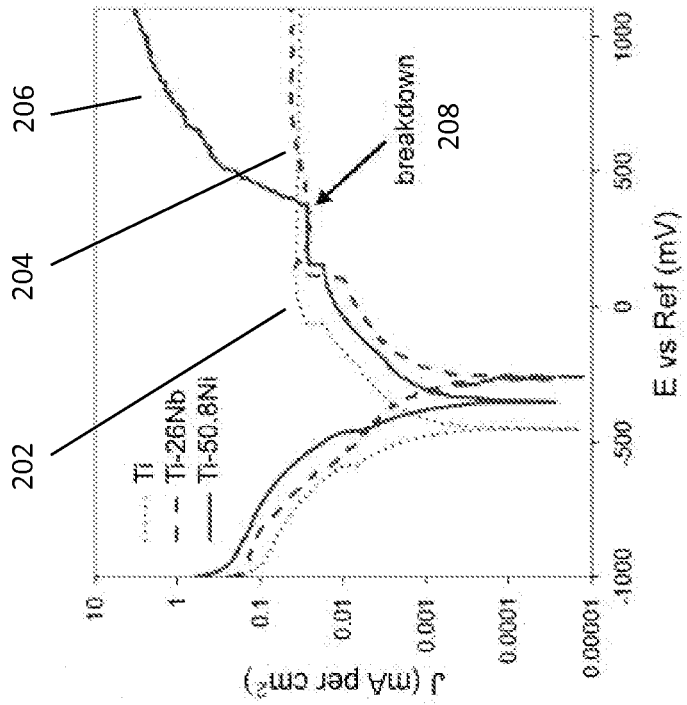

FIGS. 3A and 3B are potentiodynamic polarization graphs depicting the reaction of pure Ti 202, Ti-26Nb 204, and Ti-50.8Ni 206, in a saline (3A) and modified Hank's solution (3B) environment. Potentiodynamic tests were performed at 37° C. on $Ni_{50.8}Ti_{49.2}$, $Ti_{74}Nb_{26}$, and commercial pure Ti samples submerged in 1M NaCl or in Hank's Balanced Salt Solution (HBSS; 8 g NaCl, 0.4 g KCl, 0.14 g $CaCl_2$, 0.06 g $MgSO_4$, 0.06 g $NaH_2PO_4$, 0.35 g $NaHCO_3$, 1 g glucose, 0.6 g $KH_2PO_4$, 0.1 g $MgCl_2$ per liter de-ionized water). Corrosion resistance is a preferable property and characteristic of implantable alloys. In some cases, corrosion resistance similar to pure titanium (Ti) is desired. In order to test the corrosion resistance of each alloy, the alloys were submerged in a solution, a current was applied as indicated along the Y-axis, and a potential was measured as indicated along the X-axis. The corrosion resistance in FIG. 3A represents the effects of a corrosive environment that uses saline. FIG. 3A shows that the polarization curve of Ti-26Nb 204 immersed in 1M NaCl demonstrated a passive response similar to that of Ti over the potential range examined. In contrast, $Ni_{50.8}Ti_{49.2}$ 206 specimens submerged in 1M NaCl showed a breakdown potential at 400 mV relative to the reference electrode. Turning to FIG. 3B, Hank's modified solution, used in this test, is a balanced salt solution (HBSS) used for corrosion resistance testing because it may be applied to an instrument, implant, or to cell tissue such as allographs during the manufacture or transport of that product. As such, testing these alloys for corrosive behavior in Hank's solution may be prudent to ensure the alloys maintain integrity during processing and transport. In FIG. 3B, Hank's modified solution is used which means that the solution does not have Ca++ or Mg++. The bare surfaces of the Ti—Nb SMA did not suffer from breakdown up to 2000 mV, which may suggest that the inherent corrosion resistance of Ti—Nb is equal to or better than that of Ni—Ti. It also means that the corrosion resistance of Ti—Nb is less sensitive to surface conditions than that of Ni—Ti, and that Ti—Nb does not require the same level of stringent surface processing as needed for Ni—Ti to maintain excellent corrosion resistance. It is noted that, while the Ti—Nb—Zr alloy was not tested during the corrosion testing depicted in FIGS. 3A and 3B, it is appreciated that zirconium may be used as an alloying agent because of its corrosion resistance. As such, one skilled in the art would appreciate that adding Zr, which may be used for its corrosion resistance, to a Ti—Nb alloy that has demonstrated corrosion resistance would not negatively impact the corrosion resistance of that alloy.

Superelastic properties were evaluated from a plurality of loading-unloading cycles during experiments. Tension specimens were used to characterize the superelastic response of the materials. Specimens were loaded at a constant temperature to a certain strain level, unloaded, and then loaded again to a higher level of strain. This process continues until significant irrecoverable strain is detected after unloading, which generally occurred at 2.5% to 3% applied strain levels.

Figure 4:
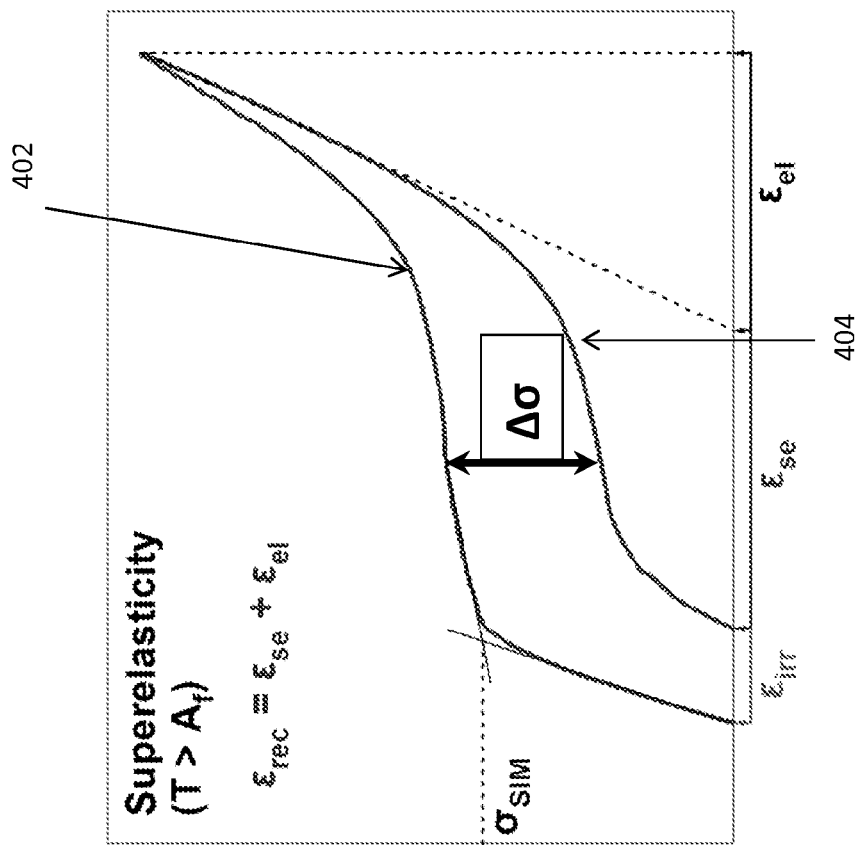
FIG. 4 is a graph of superelastic properties exhibited by Ti—Nb.
Figure 6:
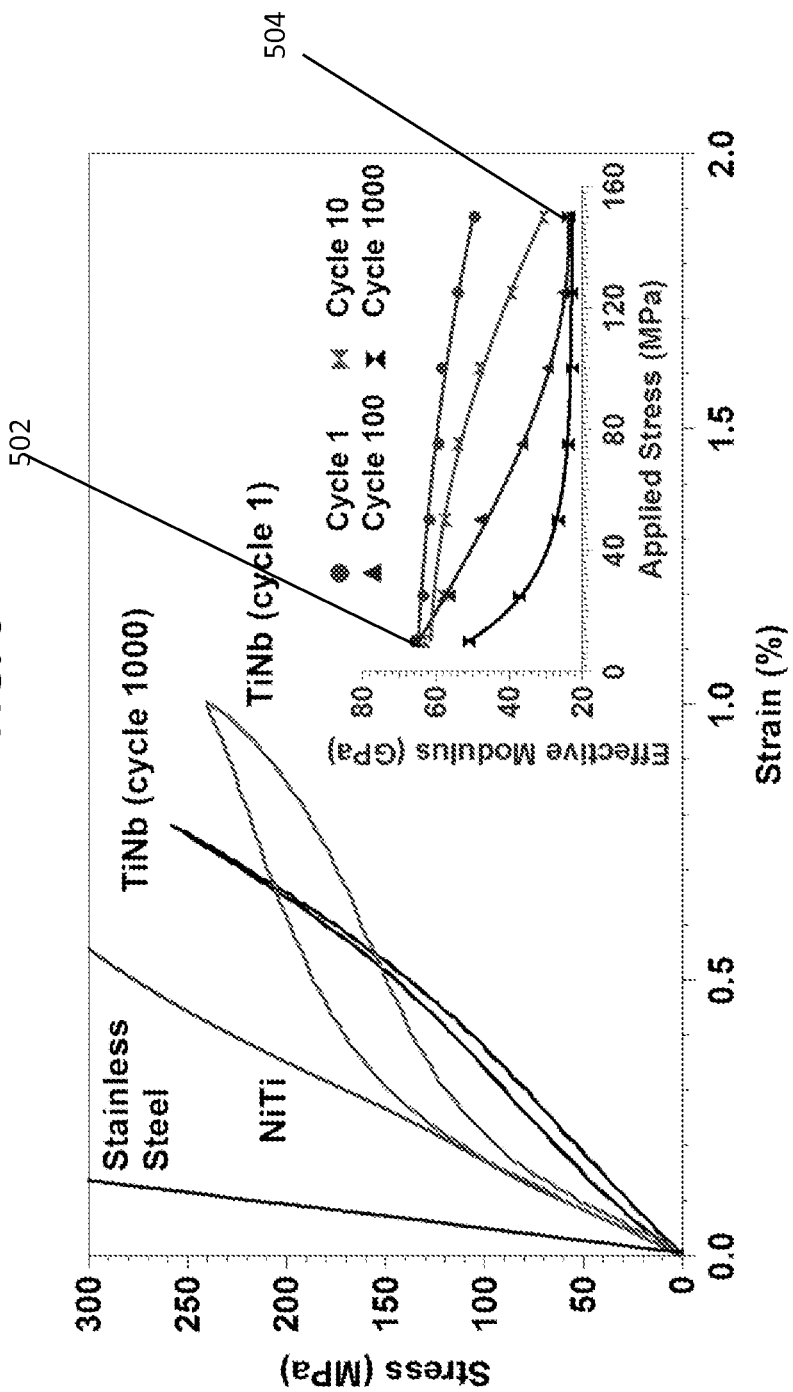
FIG. 6 is a graph of the stress-strain behavior of various alloys and an inset graph of the effect on the effective modulus of 1, 10, 100, and 1000 cycles.

FIG. 4 is a graph of superelastic properties exhibited by Ti—Nb. In FIG. 6, $\sigma_{SIM}$ denotes the critical stress for stress-induced martensitic transformation; $\epsilon_{irr}$, $\epsilon_{se}$, and $\epsilon_{el}$ represent irrecoverable strain, superelastic shape strain, and elastic recoverable strain, respectively. Total strain recovery ($\epsilon_{rec}$) in superelasticity is the sum of $\epsilon_{se}$ and $\epsilon_{el}$.

Important superelastic properties, shown in FIG. 4 are primarily irrecoverable strain ($\epsilon_{irr}$), recoverable strain ($\epsilon_{rec}$) and critical stress for stress-induced transformation ($\sigma_{SIM}$). Recoverable strain includes elastic recovery and recoverable shape change from the stress-induced martensitic transformation and possibly also martensite detwinning. With increasing applied strain, both $\epsilon_{rec}$ and $\epsilon_{irr}$ tend to increase. $\epsilon_{rec}$ reaches a maximum at some strain level while $\epsilon_{irr}$ increases monotonically with applied strain. The stress hysteresis $\Delta\sigma$ is the stress difference between the loading 402 of the stress-strain curve and the unloading 404 part of the stress-strain curve.

Figure 5:
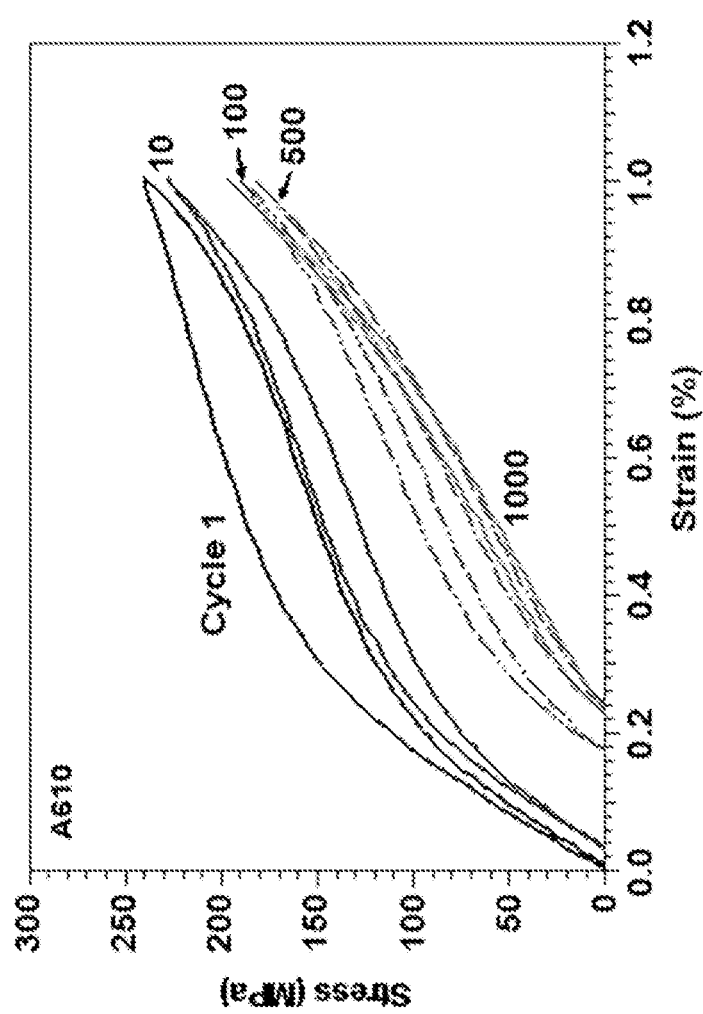
FIG. 5 is a graph of multiple stress strain curves resulting from a plurality of training processes.

FIG. 5 is a graph of multiple stress strain curves where the Ti—Nb alloy was cycled for varying numbers of cycles. During constant-temperature superelastic cycling, a number of superelastic properties changes, as demonstrated in FIG.

4. With increasing number of cycles, stress hysteresis (Δσ) decreased, and irrecoverable strain ($\epsilon_{irr}$) increased in the initial stages of cycling.

FIG. 6 is a graph of the stress-strain behavior of various alloys and the inset graph shows the effect of the applied stress level on the effective modulus of 1, 10, 100, and 1000 cycles. Also shown in FIG. 6 is the stress-strain behavior of the Ti—Nb alloy before and after cycling in comparison to other metallic materials. Prior to cycling; the elastic modulus of Ti—Nb is about 65 GPa indicated by 502, similar to that of the Ni—Ti in the austenite state, and about ⅓ of value of stainless steel. On the other hand, after 1000 cycles, the effective modulus, also referred to as the secant modulus, is further reduced 504 due to the early introduction of stress-induced phase transformation.

Cyclic Superelastic Response and Low-cycle Fatigue

Several specimens were subjected to a constant-strain, constant-temperature cyclic superelastic experiments. Here, the specimens are loaded to 1% or 1.5% strain 1000 or 1500 times at room temperature to evaluate the low-cycle functional fatigue properties of the alloys. The transformation stress ($\sigma_{SIM}$), stress hysteresis (Δσ), and irrecoverable strain ($\epsilon_{irr}$) as a function of number of superelastic cycles are summarized.

These experiments ultimately led to the creation of a method to reduce the effective elastic modulus of the disclosed alloys. The method developed combines elastic deformation with another reversible deformation mode to create a reduced effective modulus without affecting the true elastic modulus or other mechanical properties of the alloy. By combining elastic deformation and reversible stress-induced phase transformation in both the Ti—Nb and Ni—Ti shape memory alloys, an apparent effective modulus of below 30 GPa was achieved as shown in FIG. 6. Furthermore, this method enables the alloy to automatically adjust its apparent effective modulus to the properties of the surrounding bone: when the surrounding bone weakens, the apparent effective modulus of the material will be reduced in response, and vice versa.

Conventionally, a relatively high stress level is needed to trigger the stress-induced transformation. This stress level is too high for the natural load state of the body to trigger the transformation. Through superelastic cycles, it is possible to reduce the transformation stresses to very low levels. The Ti—Nb A610 alloy was cycled 1000 times at room temperature to 1% strain. As discussed above, FIG. 5 shows the resulting stress-strain curves. FIG. 6 is a comparison of the stress-strain response of stainless steel, Ni—Ti shape memory alloy, and the $Ti_{74}Nb_{26}$ A610 shape memory alloy before and after 1000 superelastic cycles. The inset shows the effective modulus (secant modulus) of the Ti—Nb SMA after various numbers of superelastic cycles as a function of stress level.

The reduced effective modulus is enabled by the stress-induced phase transformation which takes place at a very low $\sigma_{SIM}$. The effect of cycling reduced the $\sigma_{SIM}$ level at cycle 1000 to about 20 MPa, and at this point, the stress-strain curve deviates from linearity and the slope is gradually reduced. At about 75 MPa, the stress-strain curve of the cycle 1000 specimen reaches an inflection point and the slope begin to increase once again. This means that the effective modulus is not only a function of the number of superelastic cycles, but also a function of the stress level. The inset of FIG. 6 shows these relationships: as applied stress and number of superelastic cycles increase, the effective modulus drops from the original value of nearly 65 GPa to a minimum of about 22 GPa at about 75 MPa in cycle 1000. This method of modulus reduction may be referred to as "cyclic softening".

Stress shielding, as discussed above, occurs because the implant material carries a larger portion of the load than the surrounding bone, due to the higher elastic modulus of the implant. For implant constructed of conventional metals and alloys, the effect of stress shielding will naturally intensity as bone resorption and loss leads to further transfer of load to the implant, and accelerates the bone loss process. However, in the cyclically-softened Ti—Nb SMA, if bone loss occurs that leads to the transfer of more loads to the implant, the effective elastic modulus of the implant will be reduced and return the load back to the bone and preventing further degradation. The stress-dependence of the effective modulus allows the implant to adjust its properties based on its operating environment: if a higher than desired level of load is carried by the implant, it will automatically reduce its effective modulus to transfer load back to the surrounding.

Figure 7:
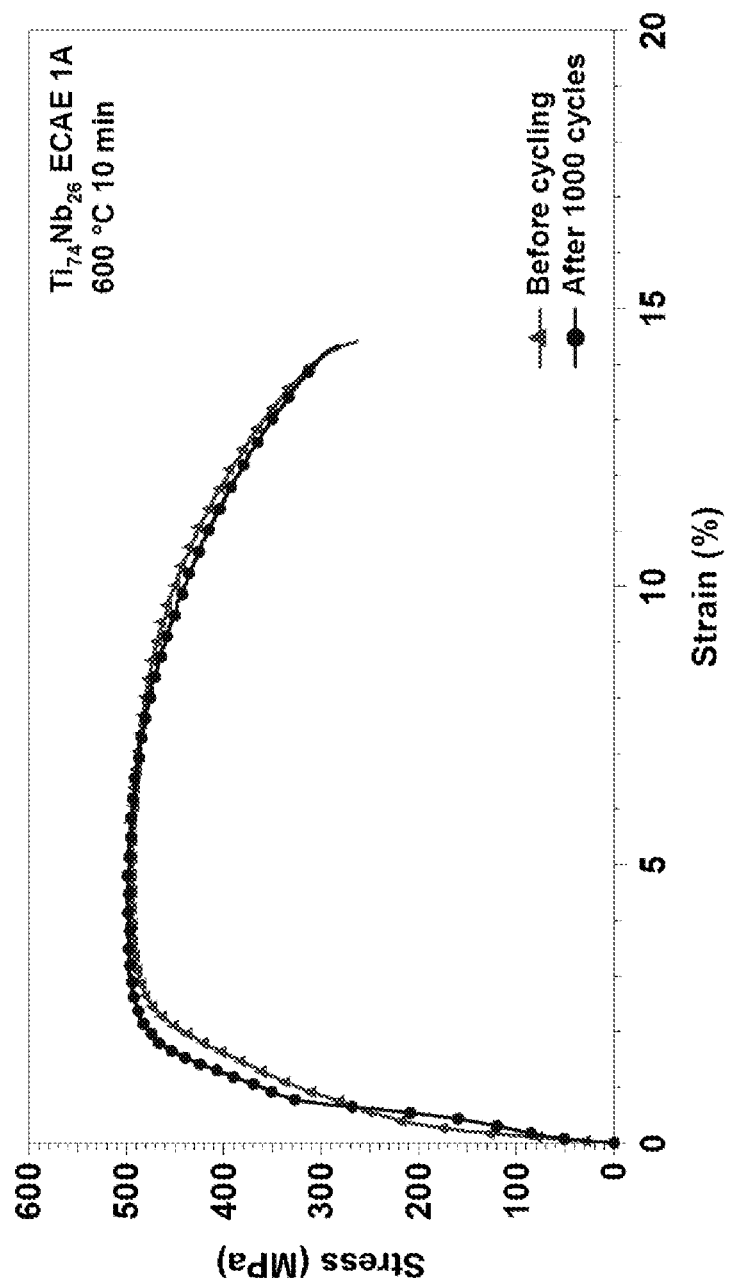
FIG. 7 is a tensile stress-strain diagram of the A610 alloy before and after 1000 superelastic cycles.

Finally, the stress-induced transformation approach, which may also be referred to as training, allows the effective modulus of the material to be reduced without affecting other mechanical properties, as shown in FIG. 7. FIG. 7 is a stress-strain diagram of the A610 alloy before and after 1000 superelastic cycles. Although cycling reduces the effective modulus, it does not affect the mechanical properties of the material. However, stress of bones in the human body from everyday activities is very difficult to measure as different bones may experience stress differently and it may vary from person to person depending on gate, age, activity level, weight, fitness level, nutrition, and other factors such as genetics. In metallic materials, the elastic modulus of a material and its ultimate strength are directly correlated, that is, stiffer materials are generally stronger. Thus the act of reducing the elastic modulus is often accompanied by a reduction in ultimate strength, and thus fatigue resistance—both parameters crucial to implants designed for long operating lifetimes. Similarly, the low elastic modulus of porous materials comes at the cost of strength as well. However, the stress-induced transformation approach does not actually change the inherent elastic constant of the material, but rather introduces a second reversible deformation mechanism to reduce the effective modulus. This means that the inherent material properties, such as strength, are not adversely affected. The effective modulus may be reduced without compromising other properties.

Figure 8A:
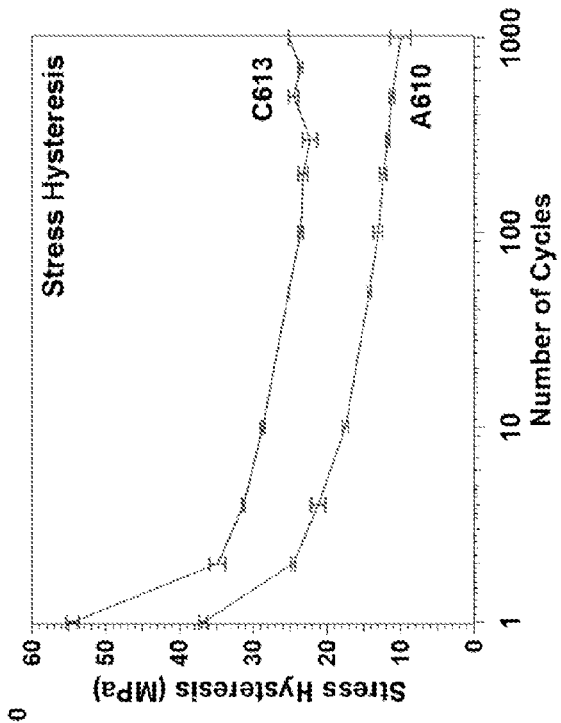
FIGS. 8A-8B are graphs that illustrate the dependence of $\sigma_{SIM}$ and stress hysteresis on the number of cycles.
Figure 8B:
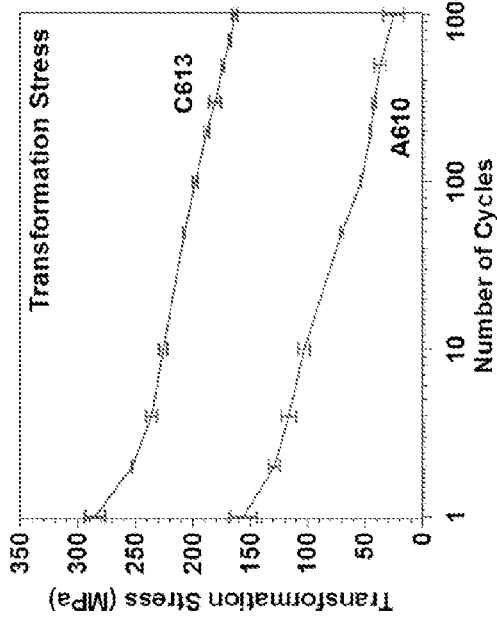

However, the effectiveness of softening may be affected by the initial condition of the alloy. FIGS. 8A-8B show the relationship between $\sigma_{SIM}$ and number of cycles in the A610 and C613 specimens. While both experiences reduction in $\sigma_{SIM}$ of C613 remains above 150 MPa after 1000 cycles. Since the reduction in effective modulus depends on reducing $\sigma_{SIM}$ to very low levels, the modulus of C613 does not change until the applied stress level exceeds 150 MPa. It should also be noted that the transformation stress values achieved through cycling are lower than what is normally possible through changing the superelastic temperature relative to the transformation temperature of the material. In the austenite state, the transformation stress is directly proportional to the temperature at which the material is deformed. Thus, if the experiment is carried out at temperatures closer to the austenite finish ($A_f$) of the material, the transformation stress is naturally lowered.

Figure 9:
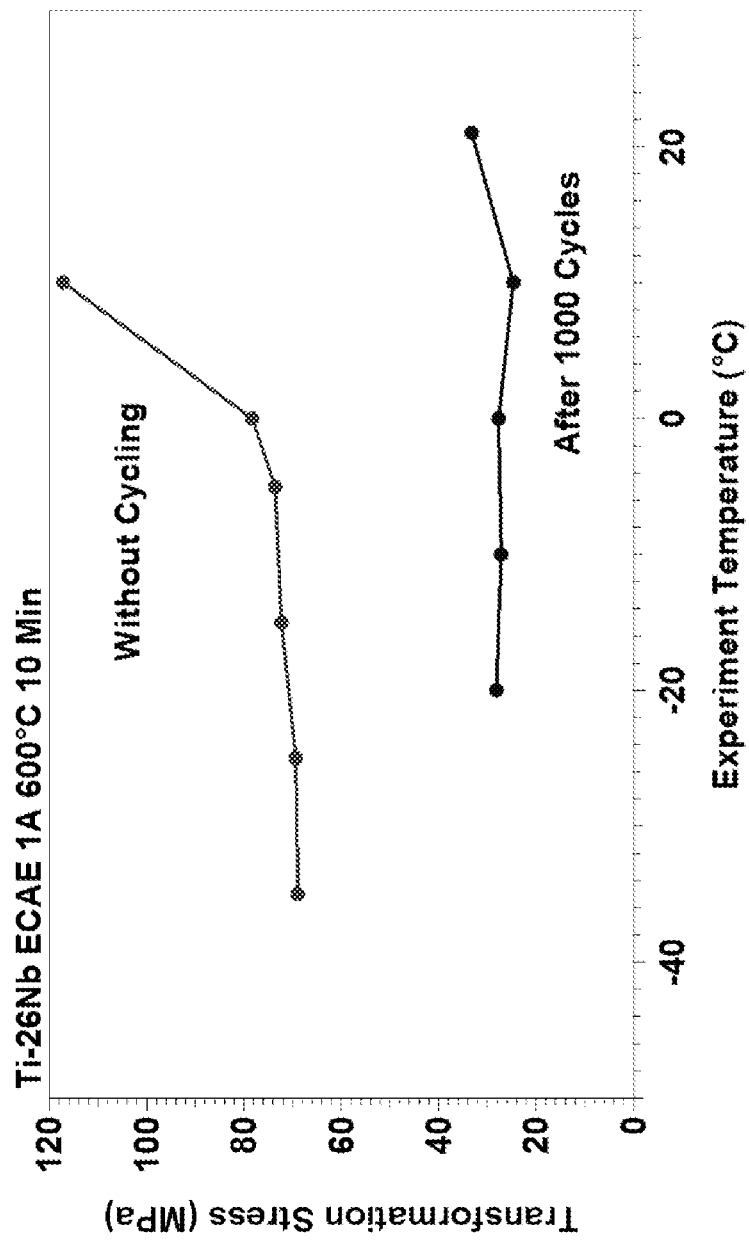
FIG. 9 is a graph that illustrates the dependence of transformation stress on the testing temperature.

This lowering is shown in FIG. 9 which shows the dependence of transformation stress on the testing temperature in the A610 specimen before and after 1000 superelastic cycles, specifically, that the transformation stress is lowered after 1000 cycles and does not spike around 12° C. like the sample tested without cycling. In FIG. 8A, $\sigma_{SIM}$ of C613 is higher than that of A610, implying that the ω precipitates, smaller grain size and higher dislocation density of C613 stabilized the austenite relative to martensite and effectively lowered the transformation temperatures of the alloy. The lower the transformation temperature, the higher the $\sigma_{SIM}$ would be at room temperature. Both precipitates and dislocations hinder the movement of martensite interface during transformation, thus increasing the total energy demand of the transformation and increasing $\sigma_{SIM}$. Simultaneously, $\sigma_{SIM}$ is also affected by the change in chemistry from precipitation. The ω precipitates are rich in titanium, so their appearance increases the niobium concentration in the matrix. A higher niobium concentration lowers transformation temperatures, which further raises $\sigma_{SIM}$ in precipitated samples. Over the course of 1000 superelastic cycles to 1% strain, the $\sigma_{SIM}$ of both specimens decreased by about 130 MPa. The initial Δσ is also higher in C613 as shown in FIG. 8B, and Δσ of both specimens decreases with increasing number of cycles. Δσ is a measure of energy dissipation and it is caused by interfacial friction and creation and/or rearrangement of defects during the martensitic transformation. The effect of defect generation and rearrangement is usually high in the first cycle, and becomes less significant with each additional cycle. Therefore, the change in Δσ is most pronounced in the first few cycles and then Δσ tends to saturate.

However, $\sigma_{SIM}$ values below 100 MPa are very difficult to achieve by changing the experiment temperature alone. By comparison, for a specimen cycled 1000 times to 1% strain, the minimum achievable transformation stress varies only weakly with testing temperature and remains much lower than the specimen without cycle at all temperatures. This means that cyclic softening is required to achieve the ultra-low elastic modulus of the material. One practical problem with the cyclic softening technique is the amount of cycles required to achieve the desired level of $\sigma_{SIM}$. It is neither economical nor practical to apply 1000 cycles individually to each device, and a simpler method is needed.

Figure 10:
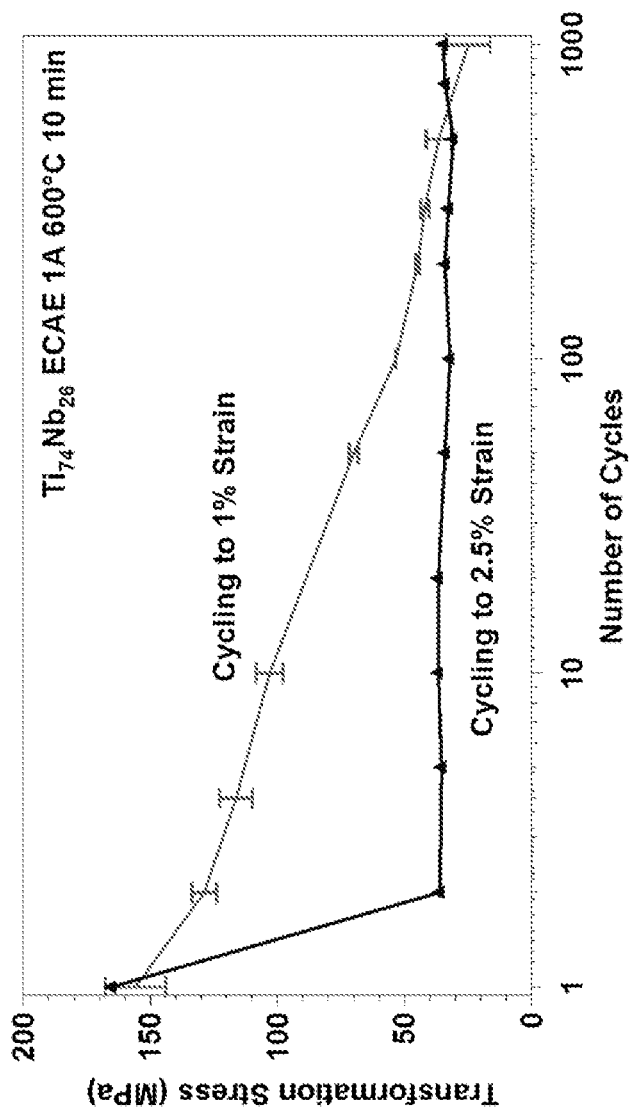
FIG. 10 is a graph that illustrates how a high number of superelastic cycles at a low strain can be replaced by a lower number of cycles at a higher strain.

FIG. 10 is a graph that illustrates how a high number of superelastic cycles at a low strain can be replaced by a lower number of cycles at a higher strain. This may be an economical way to produce the same ultra-low effective modulus with a fraction of the cycles in the training/cyclical softening process. FIG. 10 shows how 1000 superelastic cycles at 1% strain were replaced by 1 cycle at a high strain level to produce an equivalent result. When the specimen (A610) was cycled once to 2.5% strain, the transformation stress level was reduced from 150 MPa to about 30 MPa immediately, thus greatly simplifying the cyclic softening process.

Through these experiments, a stress-induced transformation technique was developed via cyclic softening to create alloys with ultra-low effective elastic modulus below 30 GPa, about half the value of the lowest reported stiffness value of 55 GPa in biomedical alloys, without negatively affecting other mechanical properties of the material. The shape of the stress-strain curve of the material further allows the material to self-adjust to the condition of the surrounding both in order to more effectively combat stress shielding. This technique may be able to be applied to all SMAs that demonstrate superelasticity.

Methods of Manufacture

Figure 11:
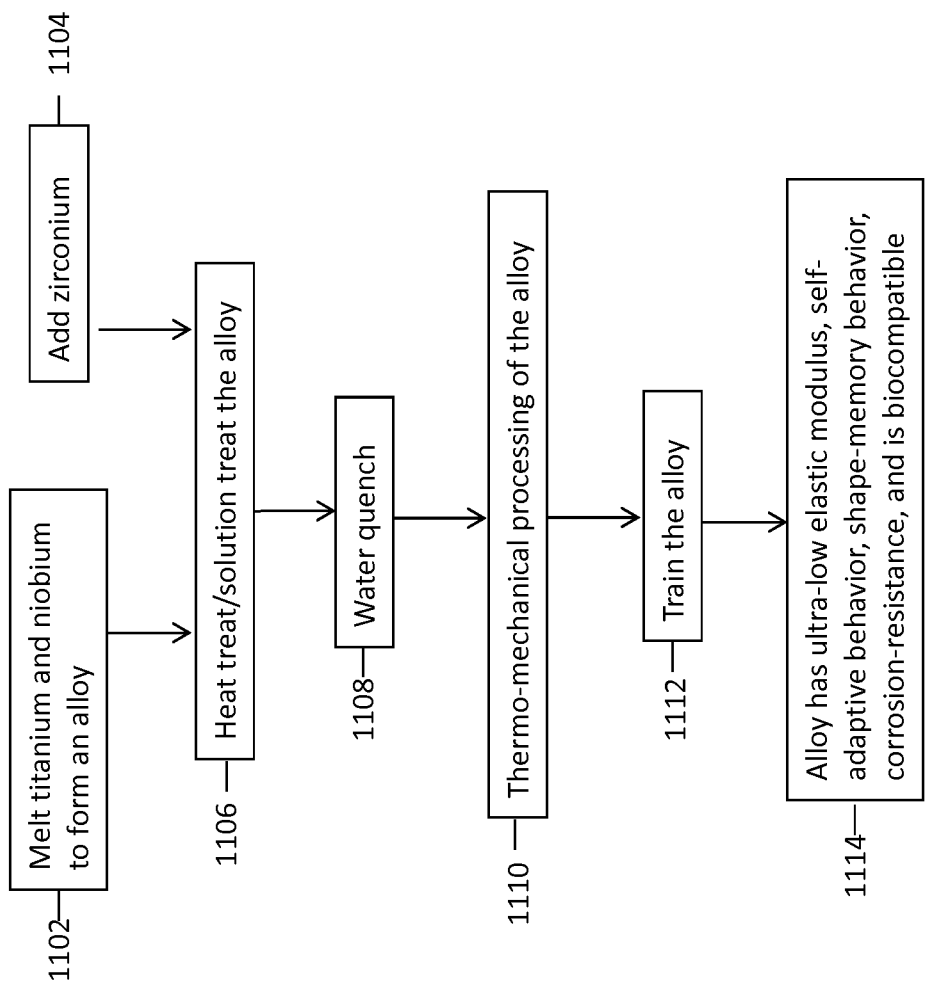
FIG. 11 is a flowchart of an embodiment of a method of manufacturing an ultra-low effective elastic modulus with shape memory properties.

FIG. 11 is a method of manufacturing an ultra-low effective elastic modulus with shape memory and superelastic properties. At block 1102, titanium (Ti) is melted with niobium (Nb) in, for example, a vacuum arc furnace. In this embodiment, the atomic percent of Nb is between 23%-26% and the balance is Ti. The alloy is then heat treated or solution treated at block 1106 which may be followed by a water quench at block 1108. In one example, the heat treatment comprises holding the alloy between 850° C.-1100° C. for a minimum of 30 minutes. In other examples, the heat treatment may comprise holding the alloy between 400° C.-800° C. or between 450° C. to 600° C. treatments 5 minutes to 60 minutes, followed by a water quench at block 1108.

Alternatively, the heat treatment at block 1106 may last from 30 minutes-72 hours. After heat treatment at block 1106, which may comprise one or more heat treatment steps and a water quench at block 1108, the alloy may be thermo-mechanically processed by hot, cold, or warm deformation including extrusion, rolling, swaging, equal channel angular extrusion, and wire drawing. The alloy may demonstrate a self-adapative, low-effective modulus response subsequent to heat treatment but prior to thermo-mechanical processing. However, the fatigue life and strength levels of those alloys may be lower than those which have been thermo-mechanically processed. Subsequent to heat treatment at block 1106 and a water quench at 1108, the alloy is thermo-mechanically processed at block 1110. The thermo-mechanical processing used at block 1110 may depend on the end application of the alloy and may comprise one or more process conducted at one or more temperatures or temperature ranges. In an embodiment, subsequent to a cold-working process, the alloy undergoes a second heat treatment process, wherein the secondheat treatment process comprises holding the alloy between 200° C. and 700° C. for at least 30 minutes and up to 100 hours While implants and orthopedics in general are discussed herein, it is noted that the alloys disclosed can be used for any application where corrosion resistance, super elasticity, self-adaptiveness, ultra-low modulus of elasticity, and shape-memory are desirable properties. This includes but is not limited to aerospace, automotive, and automation where components of a system may be subjected to corrosive environments, cyclic loading, high strains, or a combination of factors. In one example, the thermo-mechanical process comprises more than 10% of Von mises equivalent strain, and in an alternate example, the thermo-mechanical process comprises more than 50% of Von mises equivalent strain.

Turning back to FIG. 11, after the thermo-mechanical processing at block 1110, which may include post-processing heat treatment and a subsequent water quench, the alloy is trained at block 1112. Training is the process wherein a load is applied cyclically to the alloy in order to create the desired properties. This training at block 1112 may be performed at room temperature or at an elevated temperature of up to 150° C. The strain level used during training may be 1%-5% strain. It is appreciated that, as shown and discussed above in FIG. 10, in some embodiments up to 1000 superelastic cycles may be performed at 1% strain to produce an elastic modulus of about 30 GPa and in an alternate embodiment one cycle at a higher strain level such as 2.5% can also produce an equivalent modulus. In one example, the training comprises cyclic loading on the alloy to strains larger than 0.5% strain at a temperature where the alloy exhibits superelastic behavior, for example, at a temperature below 150° C. In an alternate example, the training comprises cyclic loading on the alloy to 1-3% strain at 10° C. (50° F.)-100° C. (212° F.), preferably between 20° C. (68° F.)-50° C. (122° F.). The training process at block 1112 may be dependent on the composition of the alloy as well as the desired end use. The resultant alloy at block 1114 will have corrosion resistance equivalent to pure Ti, an effective modulus of elasticity <30 GPa, and demonstrate self-adaptive, superelastic properties. It is understood as discussed above with respect to FIG. 10, that the greater the strain, the % strain, of the training, the fewer training cycles may be needed.

In an alternate embodiment, a ternary alloy, for example, zirconium, may be added at block 1104. In this example, the atomic % of Ti is between 66%-76%, the atomic % of Nb is between 20%-26% and the atomic % of Zr is between 4%-8%. In another example, the total effective content (atomic %) of Nb+Zr is between 24%-26%. In this example, for every 1% of Nb there is, there would be 0.67*Zr at % and the total of (1*Nb at %)+(0.67+Zr at %)=24%-26% total, where the balance is Ti. In either example where Zr is added at block 1104, the method in FIG. 11 proceeds as described above from blocks 1106-1114. The heat treating at block 1106 and the thermo-mechanical processing at block 1110 may proceed at above or may have varied parameters and involved more than one station at one or both block 1106 and block 1110. At block 1114, the alloy will have an effective modulus of <30 GPa and exhibits self-adaptive, shape-memory, and superelastic behavior.

Figure 12:
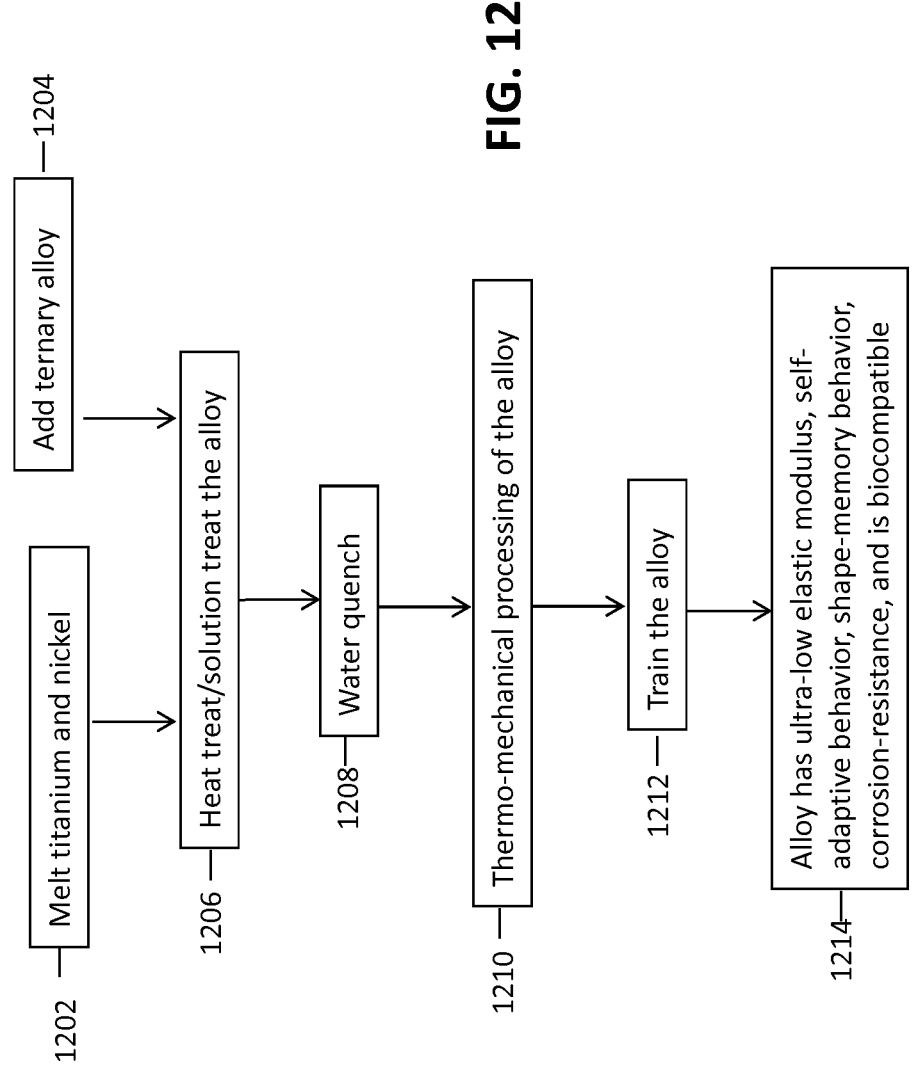
FIG. 12 is a flowchart of an alternate embodiment of a method of manufacturing a self-adaptive shape-memory alloy with an ultra-low effective modulus of elasticity.

FIG. 12 is an alternate embodiment of a method of manufacturing a self-adaptive shape-memory alloy with an ultra-low effective modulus of elasticity. At block 1202, Ti and Ni are melted under vacuum. In some embodiments, a ternary alloy is added at block 1204. In some embodiments, two components such as Ti, Ni, or the ternary alloy may be used as pre-made ingots and melted under vacuum, i.e., each type of material (metal) may be melted separately to form the alloy or two or more types of material (metals) already in ingot or other usable form may be melted with an at least an additional metal. In the absence of a ternary alloy added at block 1204, the atomic % Ni is between 49.5%-55 and the balance is Ti. The alloy formed at block 1202 is then heat treated or solution treated at block 1206 which may be followed by a water quench at block 1208. In one example, the heat treatment comprises holding the alloy between 700° C.-1100° C. for a minimum of 30 minutes. In other examples, the heat treatment may comprise holding the alloy between 400° C.-700° C. or between 250° C. to 600° C. treatments 5 minutes to 60 minutes, followed by a water quench at block 1208. Alternatively, the heat treatment at block 1206 may last from 30 minutes-100 hours. After heat treatment at block 1206, the alloy may be thermo-mechanically processed by hot, cold, or warm deformation including extrusion, rolling, swaging, equal channel angular extrusion, and wire drawing. In one embodiment, subsequent to a cold-working process, the alloy undergoes a second heat treatment process, wherein the second heat treatment process comprises holding the alloy at 200° C. to 500° C. for at least 30 minutes and up to 100 hours. It is understood that a treatment at a higher temperature may require to a shorter heat treatment time. While the experiments and findings herein were performed in a research environment, it is appreciated that processing steps that may reduce the overall processing time required to produce the desired alloy may be desired by industry for cost, safety, and efficiency purposes.

The alloy may demonstrate a self-adapative, low-effective modulus response subsequent to heat treatment but prior to thermo-mechanical processing. However, the fatigue life and strength levels of those alloys may be lower than those which have been thermo-mechanically processed. Therefore, the alloy is thermo-mechanically processed at block 1210. The thermo-mechanical processing used at block 1210 may depend on the end application of the alloy and may comprise one or more process conducted at one or more temperatures or temperature ranges. In one example, the thermo-mechanical process comprises more than 10% of the Von mises equivalent strain for the alloy system, and in an alternate example, the thermo-mechanical process comprises more than 50% of the Von mises equivalent strain.

Turning back to FIG. 12, after the thermo-mechanical processing at block 1210, the alloy is trained at block 1212. Training is the process wherein a load is applied cyclically to the alloy in order to create the desired properties. This training at block 1212 may be performed at room temperature or at an elevated temperature of up to 150° C. s. The strain level used during training may be 1%-5% strain. In one example, the training comprises cyclic loading on the alloy to strains larger than 0.5% strain at a temperature where the alloy exhibits superelastic behavior. The training process at block 1212 may be dependent on the composition of the alloy as well as the desired end use. The resultant alloy at block 1214 will have corrosion resistance equivalent to pure Ti, an effective modulus of elasticity <40 GPa, and demonstrate self-adaptive, shape-memory behavior and superelastic properties. As discussed above with respect to FIG. 10, the greater the strain, that is, the greater the % strain, used for the training, the fewer cycles may be needed.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A method of making a shape-memory alloy comprising:
   (a) melting titanium (Ti) and niobium (Nb) to form an alloy:
   (b) heat treating the alloy formed in (a);
   (c) thermo-mechanically processing the alloy: and
   (d) training the alloy via a plurality of deformation cycles to reduce an effective modulus of elasticit of the alloy below 30.0 GPa wherein (d) occurs after (c), and wherein (d) comprises cyclically subjecting the alloy to a 1-3% strain at a temperature between about 20° C. (68° F.) and about 50° C. (122° F.).

2. The method of claim 1, wherein the atomic % of Nb in the alloy is between about 23 at. % and about 26 at. %.

3. The method of claim 1, wherein (c) comprises at least one of hot-working, warm extrusion, cold extrusion, rolling, swaging, equal channel angular pressing, and wire drawing, or combinations thereof.

4. The method of claim 3, wherein the (c) comprises subjecting the alloy to a strain greater than 10% of the Von mises equivalent strain.

5. The method of claim 3, further comprising heat treating the alloy after (c) using a plurality of heat treat cycles, wherein each heat treat cycle of the plurality of heat treat cycles comprises: maintaining the alloy at a temperature between about 300° C. and about 600° C. for 5 minutes to 60 minutes followed by a water quench.

6. The method of claim 1, wherein (b) comprises maintaining the alloy at a temperature between 850° C.-1100° C. before (c).

7. The method of claim 6, wherein (b) comprises heat treating the alloy for at least 30 minutes.

8. The method of claim 1, wherein (b) further comprises water quenching the alloy after heat treating the alloy.

9. The method of claim 1, wherein (d) comprises cyclically subjecting the alloy to strains larger than 0.5% strain in the austenite phase at a temperature below 150° C.

10. A method of manufacturing a corrosion resistant, shape-memory alloy comprising:
   (a) melting titanium (Ti) and nickel (Ni) to form the alloy;
   (b) heat treating the alloy using a first heat treat process;
   (c) thermo-mechanically processing the alloy; and
   (d) training the alloy via a plurality of deformation cycles to obtain an effective modulus of elasticity less than 40 GPa.

11. The method of claim 10, wherein the atomic % of Ni is between about 49.5 at. % and about 55 at. %.

12. The method of claim 10, wherein (c) comprises at least one of hot deformation, warm deformation, or cold deformation.

13. The method of claim 12, wherein the at least one of hot, warm, or cold deformation comprises rolling, swaging, equal channel angular pressing, and wire drawing, or combinations thereof.

14. The method of claim 12, wherein the cold deformation comprises applying a strain to the alloy greater than 10% of Von mises equivalent strain.

15. The method of claim 10, wherein (b) comprises maintaining the alloy at a temperature between about 800° C. and about 1000° C. before (c).

16. The method of claim 10, wherein (b) is performed for at least 30 minutes.

17. The method of claim 10, wherein (b) is performed for 1 to 24 hrs.

18. The method of claim 10, wherein (b) is performed for 24 to 72 hrs.

19. The method of claim 10, further comprising water quenching the alloy after (c).

20. The method of claim 10, wherein the hot deformation process comprises applying a strain to the alloy greater than 50% of Von mises equivalent strain.

21. The method of claim 10, further comprising heat treating the alloy using a second heat treatment process after (c), wherein the second heat treatment process comprises maintaining the alloy at a temperature of 200° C. to 500 ° C. for 30 minutes to 100 hours.

22. The method of claim 10, wherein (d) comprises cyclically loading the alloy to 1-5% strain at a temperature between about 20° C. and about 50° C.

23. The method of claim 22, wherein the loading and unloading of the cyclical loading is performed 100-10000 times.

24. The method of claim 10, wherein (d) comprises cyclically loading the alloy to strains larger than 0.5% strain in the austenite phase at a temperature below 150° C.

25. A method of manufacturing a corrosion resistant, shape-memory alloy comprising:
   (a) melting titanium (Ti) and nickel (Ni) to form the alloy;
   (b) heat treating the alloy using a first heat treat process;
   (c) thermo-mechanically processing the alloy; and
   (d) training the alloy, to obtain an effective modulus of elasticity less than 40 GPa, wherein training the alloy comprises cyclically loading the alloy to 1-5% strain at a temperature between about 20° C. and about 50° C.

26. The method of claim 25, wherein the loading and unloading of the cyclical loading is performed 100-10000 times.

27. The method of claim 25, wherein (d) comprises cyclically loading the alloy to strains larger than 0.5% strain in the austenite phase at a temperature below 150° C.

28. A method of making a shape-memory alloy comprising:
   (a) melting titanium (Ti) and niobium (Nb) to form an alloy;
   (b) heat treating the alloy formed in (a);
   (c) thermo-mechanically processing the alloy; and
   (d) training the alloy, wherein, subsequent to training, the alloy has an effective modulus of elasticity less than 30.0 GPa, wherein training the alloy occurs after (c), and wherein training the alloy comprises cyclically subjecting the alloy to a 1-3% strain at a temperature between about 20° C. (68° F.) and about 50° C. (122° F.).

* * * * *